United States Patent [19]

Fischell et al.

[11] Patent Number: 5,484,425
[45] Date of Patent: Jan. 16, 1996

[54] RADIOPAQUE NON-KINKING THIN-WALLED INTRODUCER SHEATH

[75] Inventors: Robert E. Fischell, Dayton, Md.; Tim A. Fischell, Nashville, Tenn.

[73] Assignee: Cathco, Inc., Dayton, Md.

[21] Appl. No.: 321,806

[22] Filed: Oct. 12, 1994

Related U.S. Application Data

[63] Continuation-in-part of Ser. No. 965,961, Nov. 3, 1992, abandoned, which is a continuation-in-part of Ser. No. 517,213, May 1, 1990, Pat. No. 5,180,376.

[51] Int. Cl.⁶ .................................................. A61M 25/00
[52] U.S. Cl. ........................... 604/282; 604/169; 604/244; 604/264; 128/658
[58] Field of Search ...................... 604/95, 169, 244, 604/264, 280–283; 128/656–658, 772; 138/129–134, 139

[56] References Cited

U.S. PATENT DOCUMENTS

| | | | |
|---|---|---|---|
| 4,044,765 | 8/1977 | Kline | 128/214.4 |
| 4,676,229 | 6/1987 | Krasnicki et al. | 604/282 |
| 4,705,511 | 11/1987 | Kocak | 604/282 |
| 4,917,666 | 4/1990 | Solar et al. | 604/96 |
| 4,955,862 | 9/1990 | Sepetka | 604/282 |
| 5,180,376 | 1/1993 | Fischell | 604/282 |

*Primary Examiner*—John D. Yasko
*Assistant Examiner*—Laird J. Knights
*Attorney, Agent, or Firm*—Morton J. Rosenberg; David I. Klein

[57] ABSTRACT

This invention provides a non-kinking and thin-walled introducer sheath (10) having a flat wire metal coil (12) that lies within a plastic covering (20) fitted onto the exterior surface of the flat wire metal coil (12) and extends into a space between adjacent turns of the flat wire metal coil (12) without covering the interior surface. Each turn of the flat wire metal coil (12) has a thickness within the range between 0.75–3.0 mils with a width to thickness ratio lying between 12 and 80. A plastic adapter (30) is provided and is located at a proximal end of the sheath (10) for inserting guide wires through the sheath (10) into a vessel.

53 Claims, 3 Drawing Sheets

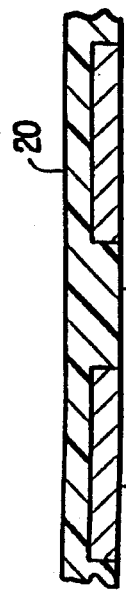
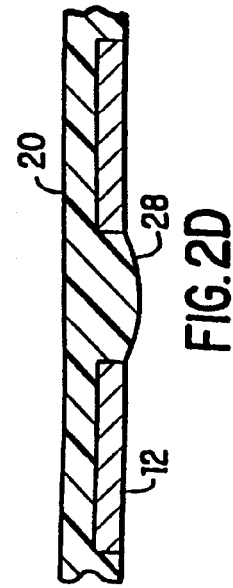
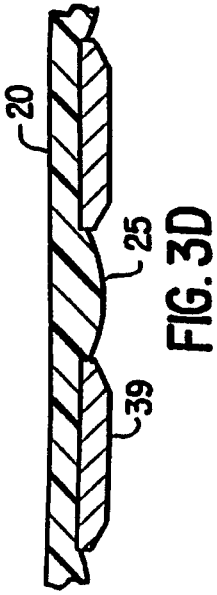
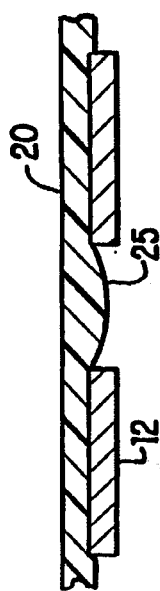
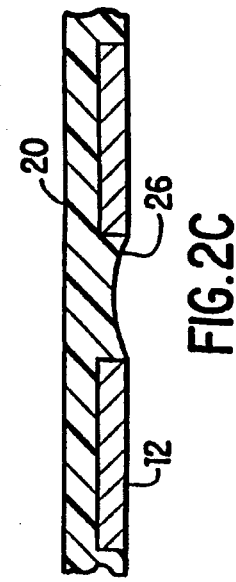
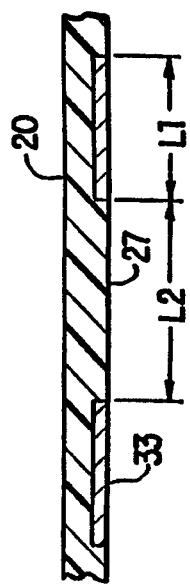
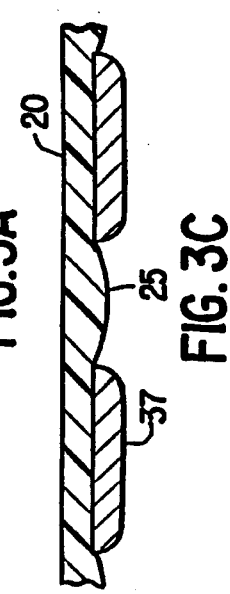

RADIOPAQUE NON-KINKING THIN-WALLED INTRODUCER SHEATH

This application is a continuation-in-part of U.S. patent application Ser. No. 07/965,961 filed 3 Nov. 1992, now abandoned, which was a continuation-in-part of U.S. patent application Ser. No. 07/517,213, filed May 1, 1990, now U.S. Pat. No. 5,180,376.

FIELD OF THE INVENTION

This invention is in the field of sheaths that pass through the skin and then enter an artery or any other vessel in a living body for the purpose of percutaneous insertion of transluminal catheters.

BACKGROUND OF THE INVENTION

It is common practice in the fields of angioplasty and atherectomy to insert catheters into the artery through a plastic sheath. These sheaths are typically made from PVC or an equivalent plastic and have a wall thickness which is typically 10 mils (1.0 mil equals 0.001 inches). One difficulty with existing sheaths is that they are so thin-walled and made from plastic so that they occasionally buckle or kink at the point where they enter into or bend in the femoral artery or where they pass through a highly curved section of an iliac artery.

It is also highly advantageous to make the sheath as thin-walled as is possible. The inner diameter of a sheath has a dimension which is controlled by the outside diameter of the catheter to be placed through it. The outside diameter of the sheath is then typically 20 mils greater than the inside diameter in order to provide a 10 mil wall of plastic which is necessary to give the sheath adequate strength. However, it would be highly advantageous to reduce the outside diameter of the sheath so as to minimize arterial distention thereby reducing the bleeding that occurs at the insertion site after the catheter and sheath are removed from the artery.

Because they are made from a thin-walled plastic, current sheaths are not significantly radiopaque. However, it would be highly advantageous to have a radiopaque sheath so that the placement of its distal end in a vessel could be easily ascertained by fluoroscopy.

SUMMARY OF THE INVENTION

It is the goal of the present invention to eliminate the shortcomings of the prior art devices in order to provide a radiopaque sheath that is non-kinking and with a thinner wall as compared with sheaths that are currently available. To achieve both a thinner wall for the sheath and to avoid kinking, this invention uses a helical metal coil for its interior which most advantageously would be fabricated from flat wire having a high ratio of wire width to wire thickness. A thin plastic covering could be coated onto and between the turns of the metal coil or the covering might be attached using heat shrinkable tubing, or by molding or extruding plastic over the thin helical metal coil. At the proximal end of the sheath is an adapter (hemostasis valve) through which the catheters are placed. This adapter would typically be molded from a plastic so as to both join onto the metal coil as well as mold onto the plastic covering of the metal coil. At its distal end, the sheath would advantageously combine a metal portion for radiopacity and at its extreme end a soft plastic tapered end piece.

Thus, it is an object of this invention to provide a sheath design which will preclude kinking while retaining good flexibility.

It is a further object of this invention to have a non-kinking sheath whose wall thickness is considerably reduced compared to the 10 mil wall thickness that is available in the devices that are now being used with balloon angioplasty catheters or atherectomy catheters.

It is still further an object of this invention that the ratio of wire width to wire thickness be greater than 12 so that a thin wall can be obtained while maintaining an adequate capability of the sheath to avoid easy crushability.

It is still further an object of this invention to have a thin-walled sheath that is radiopaque.

It is still further an object of this invention to have a smooth interior surface of the sheath that is free from sharp corners so that a catheter can readily pass through the sheath without being caught on a sharp inner edge of the metal coil wire.

It is still further an object of this invention to have a metal tip on the sheath that is highly radiopaque and that fits more closely around the dilator during introduction into the artery or vein.

It is still further an object of this invention to have a sheath with a tip comprising a cylindrical metal section for radiopacity and a soft plastic distal end piece for reducing the possibility of arterial perforation.

BRIEF DESCRIPTION OF THE DRAWING

FIG. 2A shows a wall section of the sheath with a slightly filled plastic extension in the space between adjacent turns;

FIG. 2B shows a wall section of the sheath with a completely filled plastic extension in the space between adjacent turns;

FIG. 2C shows a wall section of the sheath with an almost completely filled plastic extension in the space between adjacent turns;

FIG. 2D shows a wall section of the sheath with an over-filled plastic extension in the space between adjacent turns;

FIG. 3A shows a wall section of the sheath wherein the flat wire has rounded ends and is considerably thinner than the plastic covering and there is a greater spacing between adjacent turns;

FIG. 3B shows a wall section of the sheath wherein there is an extension of the plastic covering between adjacent turns even though the adjacent turns are touching and the flat wire is chamfered on all corners;

FIG. 3C shows a wall section of the sheath wherein only the inner corners of the flat wire metal coil are rounded;

FIG. 3D shows a wall section of the sheath wherein only the inner corners of the flat wire metal coil are chamfered;

DETAILED DESCRIPTION OF THE INVENTION

Figures 1, 6:
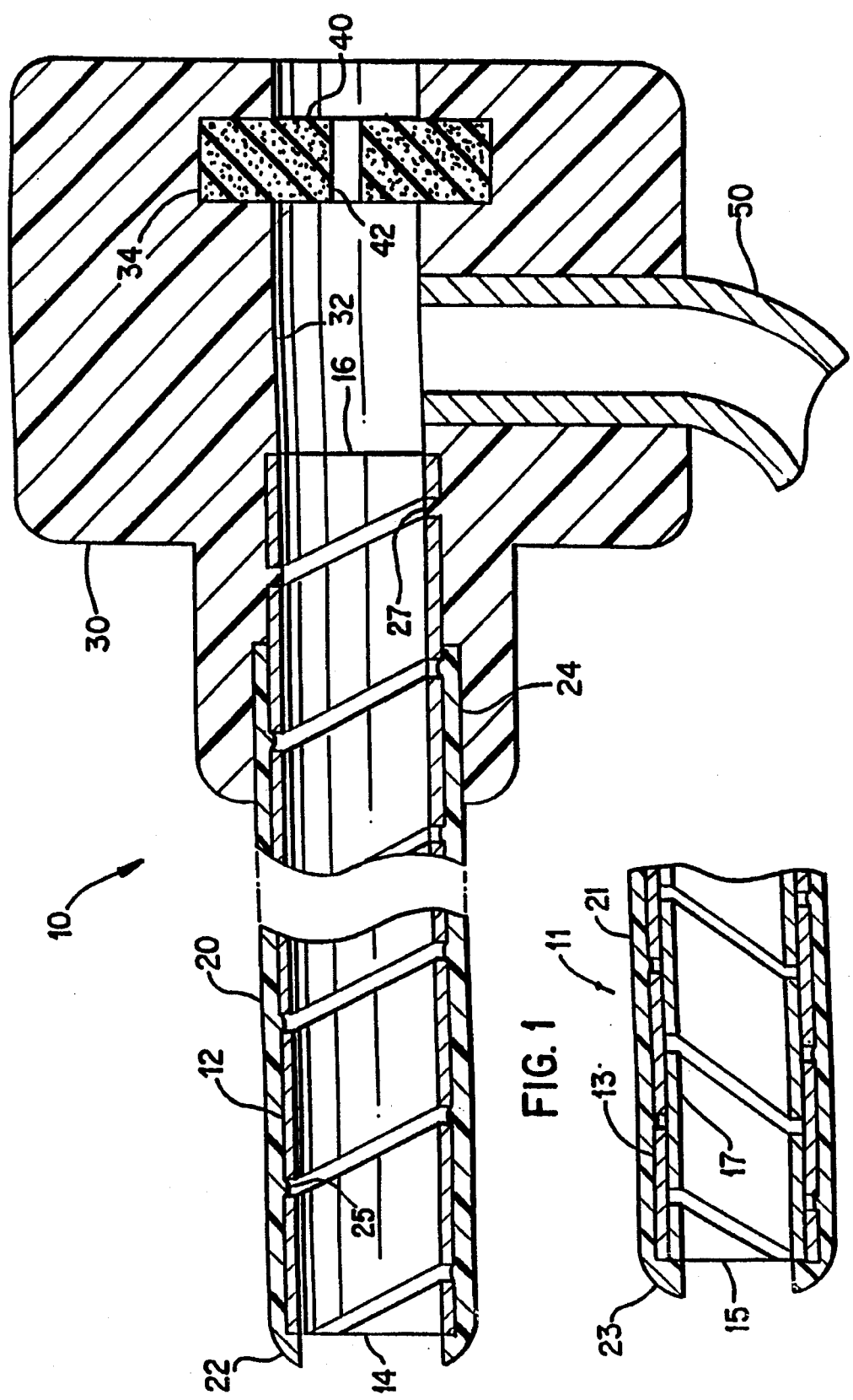
FIG. 1 is a cross-sectional view of a non-kinking, thin-walled sheath with a single helical metal coil having plastic extensions between adjacent turns.

As can be seen in FIG. 1, a non-kinking, thin-walled sheath 10 is shown with an inner metal coil 12 that lies within a plastic covering 20 for most of the length of the sheath with a plastic adapter 30 molded onto the proximal end of the sheath 10. The metal coil 12 would typically be fabricated from flat stainless steel wire or an equivalent springy metal. Metals such as 300 or 400 series stainless steel, nickel alloys such as Monel metal, or Inconel or beryllium copper, tantalum or gold alloys could be used for the flat wire metal helix material. The thickness of the wire would typically lie between 1 and 3 mils (1.0 mil= 0.001 inch) and the width of the wire would typically be between 12 to 80 times the wire thickness. This ratio of wire width to wire thickness is a very important consideration in the design of the sheath in order to prevent the sheath from collapsing while still providing a very thin wall. By actually building a model of this sheath, it has been determined that for the most desirable wire thicknesses which provide a very thin wall while preventing the sheath from collapsing in normal handling, only certain ranges of wire width to wire thickness are reasonable and these ratios are presented in TABLE 1.

The reason why very high ratios of wire width to thickness is required can be explained with the aid of FIG. 1B, which is a transverse cross-section of the wire of coil 12. The resistance to buckling of such a coil 12 when the sheath is squeezed together at a point is dependent on the so-called "section modulus" of the wire whose cross-section is shown in FIG. 1B. The section modulus (Z) is given by:

$$Z = \frac{I_x}{c} \qquad (1)$$

where $I_x$=section moment of inertia, and c=distance to the outermost fiber

For the rectangular cross-section of FIG. 1B, $$I_x = \frac{W(2c)^3}{12} = \frac{2Wc^3}{3} \qquad (2)$$

and therefore, $$Z = \frac{2Wc^2}{3} \qquad (3)$$

From equation (3) we see that to obtain the same level of stiffness to avoid crushing of the sheath, a great increase in width is necessary to offset a modest decrease in stent wire thickness. For example, if the wire thickness is halved, the wire width must be increased by a factor of 4 to maintain approximately the same crush strength of the wire coil 12. Hence, very high ratios of stent wire width to thickness, viz. in the range 12 to 80 are most advantageously required for maintaining a sufficiently high section modulus while reducing wire thickness (and therefore sheath wall thickness) to an absolute minimum. The values shown in TABLE 1 are based on the fact that for thicker wires somewhat lower ratios of width-to-thickness are allowed, but for the very thinnest wires, high ratios are required.

TABLE 1

ACCEPTABLE WIRE WIDTH-TO-THICKNESS RATIOS AS A FUNCTION OF WIRE THICKNESS

| THICKNESS RANGE (mils) | WIDTH-TO-THICKNESS RATIO |
| --- | --- |
| 1.50 to 3.00 | 12 to 50 |
| 0.75 to 1.49 | 12 to 80 |

The flat wire helix would typically be wound on a mandrel in a similar manner to the way that spring wire guides are made at the present time. Another method to form the flat wire helix would be by using machines that form tension or compression coil springs. The inner diameter of the helical coil would typically lie between 40 mils and 200 mils depending on the size of the catheter that has to be inserted through it. The distal end 14 and the proximal end 16 of the coil 12 would be typically cut off square as shown in FIG. 1.

Covering the helical coil 12 would be a plastic covering 20 having a thickness between 1 and 8 mils and which would typically be made from polyethylene, polyurethane, PVC, Surlyn or a similar plastic material. One method for forming the covering 20 so that it fits tightly around the helical coil 12 would be by sliding the coil 12 through a tube of the plastic and then heat shrinking the plastic onto the helical coil 12. Another method would be to dip coat the coil 12 into a liquid plastic material that hardens onto the helical coil 12 after dipping. Another method would be to overextrude plastic over the coil 12. A Teflon mandrel could be inserted inside the metal coil 12 before dip coating or overextruding. Whatever method is used to form the plastic covering 20, the plastic material could have a partially filled extension 25 or a fully filled extension 27, each of which projects into the space between adjacent turns of the coil. This type of structure maintains a forced separation between adjacent turns thereby preventing unwanted longitudinal displacement of one turn relative to another when the sheath 10 is severely bent. The inside diameter of either extension 25 or 27 is smaller than the outside diameter of the metal coil 12 and larger than or equal to the inside diameter of the metal coil 12.

FIGS. 2A, 2B, 2C and 2D show four sheath wall sections having four different types of plastic extensions that keep adjacent turns of coils separated from each other.

FIG. 2A is an enlarged view of the wall section of the sheath shown in FIG. 1 which has a partially filled extension 25 protruding from the plastic covering 20 which extension only slightly fills the space between adjacent turns. However, the sharp corners of the metal coil 12 prevents unwanted longitudinal displacement of the turns of the coil when the sheath is bent. This form of plastic extension is typical of that which would be obtained with heat shrinkable tubing followed by centerless grinding of the outer surface of the covering 20.

FIG. 2B shows a completely filled extension 27 of the plastic covering 20 which design is also shown in FIG. 1. This shape would typically be obtained when the plastic covering 20 is overextruded with a tight fitting cylindrical mandrel (typically made from a Teflon cylinder) placed inside the metal coil 12. The tight fitting mandrel (not shown) prevents plastic from adhering to the inner surface of the metal which, if it should occur, would result in an undesired increased wall thickness of the sheath. This type of projection could also be obtained by placing a liquid plastic material between the turns of a metal coil that has been wound on a mandrel and then placing an outer plastic covering 20 over the metal coil 12. An importance of this design is that the sharp inner corners of the flat wire are covered.

FIG. 2C shows a mostly filled extension 26 which could be formed by placing a hollow Teflon tube (not shown) inside the metal coil and then inflating the tube and then overextruding the plastic covering 20 onto and inbetween the coil 12. The Teflon tube would be deflated to allow it to be withdrawn. An importance of this design (like FIG. 2B) is that the sharp inner corners of this flat wire are covered.

FIG. 2D shows an over-filled extension 28 which could be formed by using heat shrinkable tubing for the plastic covering 20 and then heating the metal coil 12 until the metal coils "melt" into that plastic covering 20. It is also possible to overextrude the plastic covering 20 and with the appropriate type of plastic, pressure and temperature to form the plastic shape as shown in FIG. 2D. This design covers the inner corners of the flat wire and furthermore, an inner lubricity coating could be applied to the plastic to allow easier passage for an inserted catheter.

FIGS. 3A, 3B, 3C and 3D illustrate four other embodiments of wall sections for a non-kinking sheath. FIG. 3A shows an embodiment in which the flat wire metal coil 33 has a wire thickness that is considerably smaller than the thickness of the plastic covering 20. Furthermore, the coils 33 have inner and outer rounded edges. This particular wall section is shown with a plastic extension 27 similar to that shown in FIG. 2B. The width of each turn of the coil 33 is L1, and the length of the separation between turns is L2. In FIG. 3A, L2 is greater than L1. Typically, L2 would be equal to or less than L1. However, if greater flexibility is desired, L2 can be several times greater than L1. However, if L2 is greater than 1 to 2 cm, then the sheath might no longer be non-kinking. It should also be understood that a sheath might use a variable spacing L2 between adjacent turns. For example, L2 might be 0.5 mm for most of the sheath's length but L2 might be gradually increased to 5 mm at the sheath's distal end in order to increase the flexibility of the sheath's distal end.

FIG. 3B shows a wall construction in which adjacent turns are touching. However, the ends of the coils 35 are shaped so that a plastic extension 29 of the plastic covering 20 extends into the space between adjacent touching turns.

FIGS. 3C and 3D show an embodiment of the coils 37 and 39 in which there is a generally squared off outer corner at the end of each turn and a generally rounded inner corner at the end of each turn. Specifically, in FIG. 3C, the inner corners of the coil 37 are rounded and in FIG. 3D, the inner corners of the turn 39 are chamfered. It should also be understood that the outer surface of the coil could be finished so as to prevent adhesion of the plastic covering 20 to the coil; or conversely, the outer surface of the coil could be treated to cause the metal coil to bond to the plastic covering 20. Generally, adhesion or bonding of the coils outer surface to the plastic covering 20 will result in a less flexible sheath. Furthermore, increasing the ratio of L2/L1 (as seen in FIG. 3A) will increase sheath flexibility. It is well known in the wire forming art that any of the wire shapes shown in FIG. 3 could be obtained by slitting, drawing or extruding the flat wire through a die; or a combination of these methods could be used to form the desired cross-section of the generally flat wire. The cross-section of FIG. 3A could also be obtained by rolling down round wire.

The unique shapes shown in FIGS. 3C and 3D are advantageous in that their sharp outside corners dig into the plastic covering 20 thus preventing unwanted longitudinal displacement of the turns of the coil when the sheath is severely bent. Furthermore, the rounding or chamfering of the inside edge prevents the outer surface of a tight fitting catheter from being damaged by exposed sharp inner corners such as those shown in FIG. 2A as a tight fitting catheter is pushed through the sheath. Also, a tight fitting catheter would slide through the inside of the sheath with less friction or catching (especially through bends in the sheath) if the inside corners of the metal coil are rounded or chamfered as shown in FIGS. 3C and 3D. This type of wire cross-section is ideally suited for sheaths in that the outer sharp corners dig into the plastic outer plastic covering 20, thus preventing coil migration while having a smooth surface to allow easy passage of a catheter through the sheath.

It is also envisioned that any of the flat wire metal coil designs described herein could be coated with a metal or plastic so as to enhance the sheath's radiopacity or to decrease frictional forces on any catheter that would be placed through the sheath. For example, gold or tantalum plating of the flat wire would enhance the sheath's radiopacity. Furthermore, the metal coil could have a lubricity coating applied to decrease frictional forces of objects passing the sheath's interior lumen. Additionally, the bare metal could be given a thin plastic coating which would then have a lubricity coating applied. Further, there could be a very thin, separate plastic cylinder inside the metal coil. Further, as to coatings, a lubricity coating could be applied to the sheath's exterior plastic covering 20 to allow the sheath to enter human tissue and advance through human blood vessels while minimizing frictional resistance. The outer surface of the plastic covering 20 could also be treated with an anti-bacterial coating which would be especially important for sheaths that remain in a vessel for more than a few hours. Still further, the exterior plastic covering 20 could be centerless ground to make a smoother outer surface of the sheath.

In FIG. 1, we see that the distal tip 22 of the plastic covering 20 might be heat molded to an appropriate shape which can readily pass through the arterial wall with the aid of a dilator (not shown). The proximal end 24 of the covering 20 would have molded onto it a plastic adapter 30 (typically including a hemostasis valve) which can have a side-port 50 as shown in FIG. 1. The adapter 30, which may be formed from the same plastic material as the covering 20 or from another material such as PVC, would also be molded onto the proximal end of the helical coil 12. The adapter 30 would have an interior cylindrical hole 32 whose inside diameter is molded to match the inside diameter of the helical coil 12. A cylindrical groove 34 would be molded into the adapter 30 so as to accept a foam rubber packing gland or hemostasis valve 40. The packing gland 40 has a hole 42 through its center to allow for the passage of a catheter. The purpose of the gland 40 is to seal around the outside diameter of the catheter when it is in place to prevent arterial blood from escaping between the inner cylinder 32 of the adapter 30 and the outside diameter of the catheter that is percutaneously placed into the arterial system. The packing gland 40 is only indicative of more sophisticated hemostasis valves that would be used with such a sheath. An example of such a valve is shown in U.S. Pat. No. 5,041,095 by P. K. Littrell entitled "Hemostasis Valve".

As previously described, the helical coil 12 would have a wall thickness of the metal that lies between 1 and 5 mils. Similarly, the plastic covering 20 would typically have a wall thickness that lies between 1 and 5 mils. As a result, the total thickness of the coil 12 and covering 20 would be between 2 and 10 mils. At 10 mils thickness, the sheath would have the advantage of being non-kinking and radiopaque. However, it would not have any advantage in reducing the outer diameter of the sheath 10 as compared to other sheaths that are currently available. However, as we approach wire and plastic covering thicknesses on the order of 2 mils, the outer diameter of the sheath 20 is significantly reduced. There is a distinct advantage in dramatically reducing the wall thickness of the sheath 10 while at the same time having improved resistance to kinking which is provided by the strength of the helical coil 12.

Figure 4:
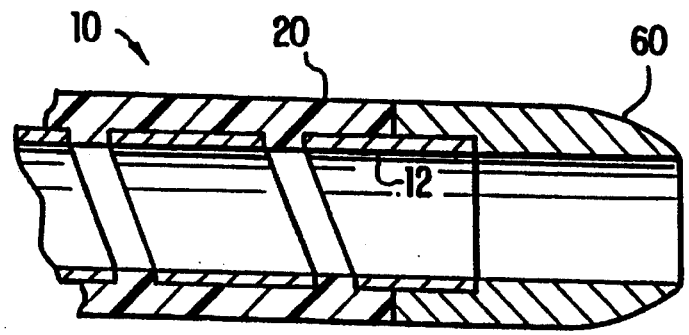
FIG. 4 is a longitudinal cross-section of the distal end of the sheath illustrating a metal tip.

FIG. 4 illustrates an improved tip design for this type of thin-walled sheath 10. As typical for this sheath design, the metal coil 12 is encased in a plastic covering 20. A metal tip 60 is joined to the coil 12 and/or covering 20 by adhesive bonding, welding or brazing or an equivalent joining means. Although a stainless steel tip could be used, a dense metal such as gold or tantalum (or an alloy of these metals) would have the advantage of greater radiopacity.

Figure 5:
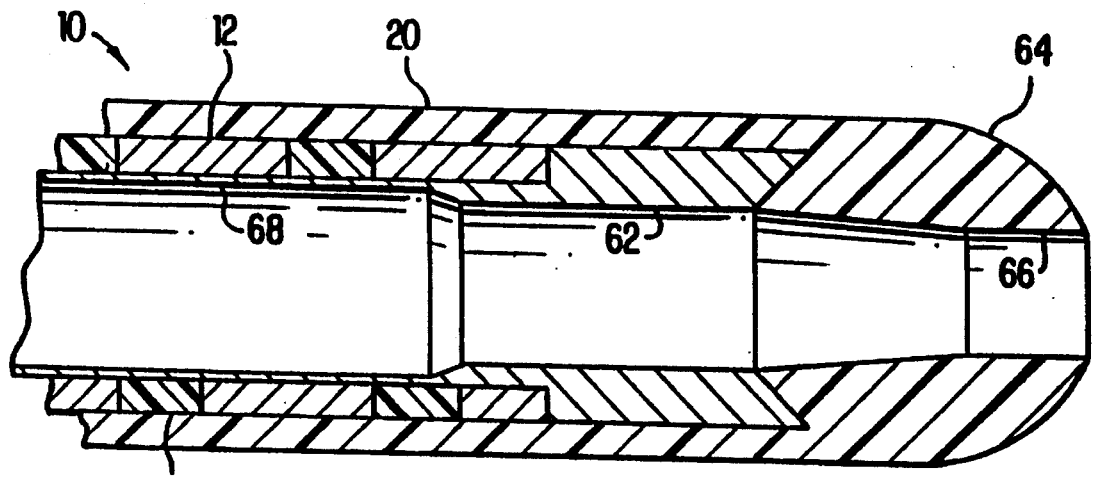
FIG. 5 is a longitudinal cross-section of the distal ends of the sheath illustrating a metal insert near the sheath's distal end and a soft plastic tip and a very thin-walled, interior tube having a lubricous coating on its interior surface; and, FIG. 6 is a cross-sectional view of the distal end of a non-kinking sheath which has two helical metal coils with a plastic extension into the space between adjacent turns of the outer coil.

FIG. 5 illustrates the distal end of a sheath 10 with a metal insert 62 joined to the coil 12 and plastic covering 20. The design of FIG. 5 would be similar to that of FIG. 4 except that a plastic tip 64 extends beyond the metal insert 62. Furthermore, the inside diameter of the insert 62 could be smaller than the inside diameter of the coil 12/and the inside diameter 66 of the plastic tip 64 could be still smaller. This design would provide a tighter fit around the dilator for improved insertion of the sheath into a vessel. Further, the soft plastic tip is potentially less damaging to the soft tissue into which the sheath plus dilator would be inserted.

FIG. 5 also shows a separate very thin-walled, plastic tube (or coating) 68 which could be placed interior to the sheath to improve lubricity. Such a tube could be advantageously made from Teflon or a different plastic with an interior surface coating to improve lubricity. Such an interior tube could be used with any tip design of the sheath. FIG. 5 also shows a separate plastic spacer 69 that lies between adjacent turns of the metal coil 12 and between the inner plastic tube 68 and the outer plastic tube 20. Thus, if desired, as many as three different plastic materials can be used for elements 20, 68 and 69 in order to optimize the properties of these three different parts of the sheath.

Although FIG. 1 shows only a single coil 12, it is envisioned that the helical coil 12 might be made from two separate metal coils, one inside the other, that are wound in opposite directions (as shown in FIG. 6) so as to improve the strength of the sheath. FIG. 6 shows the distal end of a two coil sheath 11 which has an inner helical metal coil 17, an outer helical metal coil 13 both of which are finished with a straight distal end 15. FIG. 6 also shows a plastic covering 21 with a molded distal end 23 which design is similar to FIG. 1. A FIG. 6 type design in which the inner metal coil is nominally 2 mils thick, the outer metal coil is nominally 2 mils thick and the plastic covering is also 2 mils, would achieve a non-kinking sheath design which still has a significant wall thickness reduction as compared to sheaths that are currently available.

All the sheath designs described herein have metal coils which are intrinsically radiopaque. Hence, these sheath designs have the additional functional attribute of being radiopaque even without the addition of highly radiopaque distal tips.

The possibility of a very thin plastic coating or plastic tube on the interior surface of the inside metal coil is also envisioned for these sheath designs as shown in FIG. 5. Such a coating or plastic tube would optimally have a very low coefficient of friction.

Although the utilization of sheaths in arteries is described herein in considerable detail, the sheath that is taught herein is also able to be used for access to a variety of lumens of humans or animals, such as veins, urethras, fallopian tubes, biliary ducts, bronchial tubes or any similar vessel in a living body.

Various other modifications, adaptations, and alternative designs are of course possible in light of the above teachings. Therefore, it should be understood at this time that within the scope of the appended claims, the invention may be practiced otherwise than as specifically described herein.

What is claimed is:

1. An introducer sheath for percutaneous insertion into a vessel of a human body comprising:
    (a) a flat wire metal coil having a distal end and a proximal end and having some separation defining a space between adjacent turns of the flat wire metal coil, the interior surface of said flat wire metal coil forming an interior lumen of the sheath;
    (b) a plastic covering that is fitted onto and is in contact with the exterior surface of said flat wire metal coil, said plastic covering extending into the space between each of said adjacent turns of the flat wire metal coil without covering the interior surface of the flat wire metal coil whereby said separation between all of said adjacent turns of said flat metal coil is maintained when said introducer sheath is bent, each of said turns of said flat wire metal coil having a predetermined thickness within the approximate range of 0.75 to 3.0 mils with a predetermined width to thickness ratio between 12 and 80; and,
    (c) a plastic adapter including a hemostasis valve located at the proximal end of the sheath for inserting guide wires and/or catheters through the sheath and into a vessel of the human body.

2. The sheath of claim 1 wherein the flat wire metal coil is made from stainless steel.

3. The sheath of claim 2 wherein the flat wire metal coil is made from a 300 series stainless steel.

4. The sheath of claim 2 wherein the flat wire metal coil is made from 400 series stainless steel.

5. The sheath of claim 1 wherein the flat wire metal coil has a space between adjacent turns that is less than the width of a single turn of the coil.

6. The sheath of claim 1 wherein the flat wire metal coil has a space between adjacent turns that is larger than the width of a single turn of the coil.

7. The sheath of claim 1 wherein the space between adjacent turns of said flat wire metal coil is less than 5.0 mm.

8. The sheath of claim 1 wherein the space between said adjacent turns is fixed.

9. The sheath of claim 1 wherein the space between said adjacent turns is variable.

10. The sheath of claim 9 wherein the space between said adjacent turns is greater at the sheath's distal end as compared to a more proximal portion of the sheath so that the sheath's tip is more flexible.

11. The sheath of claim 9 wherein the sheath has a more flexible proximal section where it passes through the skin and into an artery.

12. The sheath of claim 1 wherein the flat wire metal coil is plated with a dense metal such as gold or tantalum.

13. The sheath of claim 1 wherein the flat wire metal coil has an interior lubricious coating.

14. The sheath of claim 1 wherein said adjacent turns are touching at a radial dimension which is less than the radial dimension to the exterior surface of the flat wire metal coil and wherein there is some space between said adjacent turns that allows some outer plastic covering to extend into said space.

15. The sheath of claim 1 wherein the sheath is formed by heat shrinking the plastic covering over the metal coil.

16. The sheath of claim 1 wherein the sheath is formed by first dilating the plastic covering with a solvent and then allowing the evaporation of the solvent to cause the covering to shrink around the flat wire metal coil.

17. The sheath of claim 1 wherein the plastic covering is an elastomer.

18. The sheath of claim 17 wherein the plastic covering is a polyethylene.

19. The sheath of claim 17 wherein the plastic covering is a polyurethane.

20. The sheath of claim 17 wherein the plastic covering is polyvinylchloride.

21. The sheath of claim 17 wherein the plastic covering is Teflon.

22. The sheath of claim 1 wherein the thickness of the plastic covering is less than 0.005 inches.

23. The sheath of claim 1 wherein the plastic covering is centerless ground on its exterior surface to provide a smoother finish on that exterior surface.

24. The sheath of claim 1 wherein the sheath is formed by overextruding plastic over the flat wire metal coil.

25. The sheath of claim 24 wherein the sheath is formed by overextruding plastic over the flat wire metal coil, a central mandrel having been inserted into said coil prior to the overextrusion of plastic.

26. The sheath of claim 1 wherein the sheath is formed by coating the plastic covering over the metal coil by dipping the coil into a liquid material.

27. The sheath of claim 1 wherein the flat wire metal coil is formed from a flat wire whose cross section has squared off ends.

28. The sheath of claim 1 wherein the flat wire metal coil is formed from flat wire whose cross section has all corners rounded.

29. The sheath of claim 1 wherein the flat wire metal coil is formed from a flat wire whose cross section has all corners chamfered.

30. The sheath of claim 1 wherein the flat wire metal coil is formed from flat wire having only the interior corners of its cross section rounded.

31. The sheath of claim 1 wherein the flat wire metal coil is formed from flat wire having only the interior corners of its cross section chamfered.

32. The sheath of claim 1 wherein the outer surface of the flat wire metal coil does not adhere to the plastic covering.

33. The sheath of claim 1 wherein the plastic covering has an extension which projects into the space between said adjacent turns but does not completely fill that space which space is bounded on its interior by the inside diameter of the flat wire metal coil.

34. The sheath of claim 1 wherein the plastic covering has an extension which projects into and completely fills the space between adjacent turns of the flat wire metal coil so that the inside diameter of the plastic extension is essentially equal to the inside diameter of the flat wire metal coil.

35. The sheath of claim 1 wherein the plastic covering has an extension which projects into the space between adjacent turns of the flat wire metal coil with the inside diameter of the extension being smaller than the inside diameter of said flat wire metal coil without any plastic covering the interior surface of the flat wire metal coil.

36. The sheath of claim 1 wherein the plastic covering has a lubricity coating applied to its outer surface.

37. The sheath of claim 1 wherein the inner surface of the plastic extension between adjacent turns has a lubricity coating applied.

38. The sheath of claim 1 wherein a metal tip is placed at the sheath's distal end.

39. The sheath of claim 38 wherein the metal tip is made from a high density, radiopaque metal.

40. The sheath of claim 39 wherein the tip is formed from a dense metal at least some of said metal being tantalum.

41. The sheath of claim 39 wherein the tip is formed from a dense metal at least some of which said metal being gold.

42. The sheath of claim 1 wherein a metal insert is placed near the sheath's distal end with a plastic covering extending distally beyond the metal insert.

43. The sheath of claim 1 wherein the sheath includes a metal tip at its distal end whose inside diameter is less than the inside diameter of the flat wire metal coil.

44. The sheath of claim 1 wherein the sheath includes a metal insert near its distal end whose inside diameter is less than the inside diameter of the flat wire metal coil.

45. The sheath of claim 1 wherein the sheath includes a plastic tip whose inside diameter is less than the inside diameter of the flat wire metal coil.

46. The sheath of claim 1 wherein the sheath includes a side port in the plastic adapter near the sheath's proximal end.

47. The sheath of claim 1 wherein the distal tip of the plastic covering extends beyond the distal end of the flat wire metal coil and is heat molded to an appropriate shape which can readily pass through the arterial wall.

48. The sheath of claim 1 wherein an interior plastic tube having a thickness of less than 0.004 inches is inserted interior to the flat wire metal coil.

49. The sheath of claim 48 wherein the interior plastic tube is made from Teflon.

50. The sheath of claim 48 wherein the interior plastic tube has a lubricity coating applied to its interior surface.

51. The sheath of claim 1 wherein the anti-bacterial coating is applied to the sheath's outer plastic covering.

52. An introducer sheath for percutaneous insertion into a vessel of a human body comprising:

(a) a flat wire metal coil having a distal end and a proximal end and having some separation between adjacent turns of the flat wire metal coil, each of said turns of said flat wire metal coil having a predetermined thickness within the approximate range of 0.075 to 3.0 mils with a predetermined width to thickness ratio between 12 and 20;

(b) a plastic covering that is fitted onto and is in contact with the exterior surface of said flat wire metal coil, said plastic covering extending into the space between said adjacent turns of the flat wire metal coil without covering the interior surface of the flat wire metal coil;

(c) an inner plastic tubular member having a through passage forming an interior lumen of said sheath, said inner plastic tubular member being positionally located contiguous an interior surface of said flat wire metal coil; and, (d) a plastic adapter including a hemostasis valve located at the proximal end of said sheath for inserting guide wires and/or catheters through said sheath and into a vessel of the human body.

53. An introducer sheath for percutaneous insertion into a vessel of a human body comprising:

(a) a flat wire metal coil having a distal end and a proximal end and having some separation defining interstices between adjacent turns of the flat wire metal coil, the interior surface of said flat wire metal coil forming an interior lumen of the sheath;

(b) a plastic covering fitted onto and in contact with the exterior surface of said flat wire metal coil;

(c) an inner plastic tubular member having a through passage forming an interior lumen of said sheath, said inner plastic tubular member being positionally located contiguous an interior surface of said flat wire metal coil;

(d) a plurality of plastic insert members inserted within said interstices; and, (e) a plastic adapter including a hemostasis valve located at the proximal end of the sheath for inserting guide wires and/or catheters through the sheath and into a vessel of the human body.

* * * * *